United States Patent
Smart et al.

(10) Patent No.: US 7,310,543 B2
(45) Date of Patent: Dec. 18, 2007

(54) SILICON MICROPROBE WITH INTEGRATED BIOSENSOR

(75) Inventors: Wilson Smart, Palo Alto, CA (US); Kumar Subramanian, Pleasanton, CA (US); Eugene Orloff, Berkeley, CA (US)

(73) Assignee: Kumetrix, Inc., Union City, CA (US)

( * ) Notice: Subject to any disclaimer, the term of this patent is extended or adjusted under 35 U.S.C. 154(b) by 0 days.

(21) Appl. No.: 09/816,472

(22) Filed: Mar. 26, 2001
(Under 37 CFR 1.47)

(65) Prior Publication Data

US 2002/0137998 A1    Sep. 26, 2002

(51) Int. Cl.
*A61B 5/05*    (2006.01)
(52) U.S. Cl. .................. 600/345; 600/347; 600/365
(58) Field of Classification Search ......... 600/345–350
See application file for complete search history.

(56) References Cited

U.S. PATENT DOCUMENTS

| | | | |
|---|---|---|---|
| 2,359,550 A | 10/1944 | Eriksen | |
| 3,046,987 A | 7/1962 | Ehrich | |
| 3,640,267 A | 2/1972 | Hurtig et al. | |
| 3,640,388 A | 2/1972 | Ferrari | |
| 3,640,393 A | 2/1972 | Hurtig | |
| 3,799,742 A | 3/1974 | Coleman | |
| 4,627,445 A | 12/1986 | Garcia et al. | |
| 4,637,403 A | 1/1987 | Garcia et al. | |
| 4,790,979 A | 12/1988 | Terminiello et al. | |
| 4,837,049 A | 6/1989 | Byers et al. | |
| 4,873,993 A | 10/1989 | Meserol et al. | |
| 4,995,402 A | 2/1991 | Smith et al. | |
| 5,014,718 A | 5/1991 | Mitchen | |
| 5,029,583 A | 7/1991 | Meserol et al. | |
| 5,035,704 A | 7/1991 | Lambert et al. | |
| 5,054,499 A | 10/1991 | Swierczek | |
| 5,192,502 A | 3/1993 | Attridge et al. | |
| 5,217,480 A | 6/1993 | Haber et al. | |
| 5,231,993 A | 8/1993 | Haber et al. | |
| 5,284,567 A | 2/1994 | Matson | |
| 5,290,420 A | 3/1994 | Matson | |
| 5,513,636 A * | 5/1996 | Palti ........................ | 600/345 |
| 5,514,152 A | 5/1996 | Smith | |
| 5,540,709 A | 7/1996 | Ramel | |
| 5,582,184 A | 12/1996 | Erickson et al. | |
| 5,591,139 A | 1/1997 | Lin et al. | |
| 5,636,640 A | 6/1997 | Staehlin | |

(Continued)

FOREIGN PATENT DOCUMENTS

DE    35 15 420 AI    10/1986

(Continued)

OTHER PUBLICATIONS

Smart, W.H., et al. "The Use of Silicon Microfabrication Technology in Painless Blood Glucose Monitoring" *Diabetes Technology & Therapeutics*, vol. 2, No. 4, Winter 2000, USA.

(Continued)

*Primary Examiner*—Robert L. Nasser

(57) ABSTRACT

Microprobe device 10 provides an analyte signal from biosensor 12 to an external analyte meter indicating analyte presence in an analyte-containing bodily fluid of a subject (not shown).

42 Claims, 6 Drawing Sheets

U.S. PATENT DOCUMENTS

| | | | |
|---|---|---|---|
| 5,660,163 A | 8/1997 | Schulman et al. | |
| 5,682,233 A | 10/1997 | Brinda | |
| 5,746,217 A | 5/1998 | Erickson et al. | |
| 5,770,369 A * | 6/1998 | Meade et al. | 435/6 |
| 5,801,057 A | 9/1998 | Smart et al. | |
| 5,820,570 A | 10/1998 | Erickson et al. | |
| 5,855,801 A | 1/1999 | Lin et al. | |
| 5,871,494 A | 2/1999 | Simons et al. | |
| 5,928,207 A | 7/1999 | Pisano et al. | |
| 5,938,679 A | 8/1999 | Freeman et al. | |
| 6,048,352 A | 4/2000 | Douglas et al. | |
| 6,051,392 A | 4/2000 | Ikdeda et al. | |
| 6,091,975 A * | 7/2000 | Daddona et al. | 600/345 |
| 6,099,484 A | 8/2000 | Douglas et al. | |
| 6,106,751 A | 8/2000 | Talbot et al. | |
| 6,120,676 A | 9/2000 | Heller et al. | |
| 6,134,461 A * | 10/2000 | Say et al. | 600/345 |
| 6,152,889 A | 11/2000 | Sopp et al. | |
| 6,180,062 B1 | 1/2001 | Naka et al. | |
| 6,201,980 B1 | 3/2001 | Darrow et al. | |
| 6,206,841 B1 | 3/2001 | Cunningham et al. | |
| 6,235,539 B1 | 5/2001 | Carpenter | |
| 6,259,937 B1 | 7/2001 | Schulman et al. | |
| 6,283,926 B1 | 9/2001 | Cunningham et al. | |
| 6,284,478 B1 | 9/2001 | Heller et al. | |
| 6,306,104 B1 | 10/2001 | Cunningham et al. | |
| 6,332,871 B1 | 12/2001 | Douglas et al. | |
| 6,349,230 B1 * | 2/2002 | Kawanaka et al. | 600/345 |
| 6,358,265 B1 | 3/2002 | Thorne, Jr. et al. | |
| 6,360,888 B1 | 3/2002 | McIvor et al. | |
| 6,364,890 B1 | 4/2002 | Lum et al. | |
| 6,375,627 B1 | 4/2002 | Mauze et al. | |
| 6,405,066 B1 | 6/2002 | Essenpreis et al. | |
| 6,442,413 B1 | 8/2002 | Silver | |
| 6,561,989 B2 | 5/2003 | Whitson | |
| 6,572,566 B2 | 6/2003 | Effenhauser | |
| 6,592,815 B1 | 7/2003 | Zimmer | |
| 6,612,111 B1 * | 9/2003 | Hodges et al. | 60/583 |
| 6,783,502 B2 | 8/2004 | Orloff et al. | |
| 6,866,675 B2 | 3/2006 | Perez et al. | |
| 2002/0004196 A1 | 1/2002 | Whitson | |
| 2002/0168290 A1 | 11/2002 | Yuzhakov et al. | |
| 2002/0169470 A1 | 11/2002 | Kuhr et al. | |
| 2003/0018282 A1 | 1/2003 | Effenhauser et al. | |
| 2003/0028087 A1 | 2/2003 | Yuzhakov et al. | |
| 2003/0028125 A1 | 2/2003 | Yuzhakov et al. | |
| 2003/0050573 A1 | 3/2003 | Kuhr et al. | |
| 2003/0144608 A1 | 7/2003 | Kojima et al. | |
| 2003/0171699 A1 | 9/2003 | Brenneman | |
| 2003/0211619 A1 | 11/2003 | Olson et al. | |
| 2003/0212344 A1 | 11/2003 | Yuzhakov et al. | |
| 2003/0212345 A1 | 11/2003 | McAllister et al. | |
| 2003/0212346 A1 | 11/2003 | Yuzhakov et al. | |
| 2003/0212347 A1 | 11/2003 | Sohrab | |
| 2003/0223906 A1 | 12/2003 | McAllister et al. | |
| 2004/0096959 A1 | 5/2004 | Stiene et al. | |
| 2004/0106941 A1 | 6/2004 | Roe et al. | |
| 2004/0127818 A1 | 7/2004 | Roe | |
| 2004/0127819 A1 | 7/2004 | Roe et al. | |
| 2004/0186394 A1 | 9/2004 | Roe et al. | |
| 2004/0193072 A1 | 9/2004 | Allen | |
| 2004/0193202 A1 | 9/2004 | Allen | |
| 2004/0236250 A1 | 11/2004 | Hodges et al. | |
| 2005/0033341 A1 | 2/2005 | Vreeke et al. | |
| 2005/0139489 A1 | 6/2005 | Davies et al. | |

FOREIGN PATENT DOCUMENTS

| | | |
|---|---|---|
| DE | 197 53 849 | 6/1999 |
| DE | 19753847 | 6/1999 |
| DE | 19753849 | 6/1999 |
| EP | 0 127 958 A2 | 5/1984 |
| EP | 0 199 484 B1 | 10/1986 |
| EP | 0 565 970 B1 | 6/1994 |
| EP | 0 723 418 B1 | 7/1996 |
| EP | 1 034 740 AI | 9/2000 |
| EP | 1 035 921 B1 | 9/2000 |
| EP | 1 374 770 A1 | 2/2003 |
| FR | 2 590 673 | 5/1987 |
| GB | 0030929.4 | 1/2002 |
| JP | 02-120655 | 5/1990 |
| JP | 04194660 A1 | 7/1992 |
| JP | 09 084781 | 9/1995 |
| JP | 09-089885 | 4/1997 |
| JP | 09-168530 | 6/1997 |
| JP | 09-285459 | 11/1997 |
| JP | 09-294737 | 11/1997 |
| WO | WO 8504089 | 9/1985 |
| WO | WO 861005 | 1/1986 |
| WO | WO 91//6855 AI | 5/1991 |
| WO | WO 93/09710 A1 | 5/1993 |
| WO | WO 96/00614 A | 1/1996 |
| WO | WO 97/42888 | 11/1997 |
| WO | WO 98/35225 AI | 8/1998 |
| WO | WO 00/04832 | 2/2000 |
| WO | WO 01/72220 A1 | 10/2001 |
| WO | WO 01/93930 A1 | 12/2001 |
| WO | WO 02/49507 A1 | 6/2002 |
| WO | WO 02/056769 A1 | 7/2002 |
| WO | WO 2004/064636 A1 | 8/2004 |

OTHER PUBLICATIONS

Steinkuhl, R. et al., "Glucose Sensor in Containment Technology", *Horm. Metab. Res.* 1994, pp. 531-533 v. 26, Georg Thieme Verlag Stuttgart, New York.

Abdel-Hamid, Ihab et al., "Development of a Needle-type Biosensor for Intravascular Glucose Monitoring", *Analytica Chimica Acta*, 1995, pp. 45-54, v. 313, Elsevier Science BV, Netherlands.

Kim, Youn Tae, "Needle-Shaped Glucose Sensor with Multi-Cell Electrode Fabricated by Surface Micromachining, Proceedings of SPIE", 1999, pp. 924-930, vol. 3680 Part 2, *The International Society for Optical Engineering*, U.S.

* cited by examiner

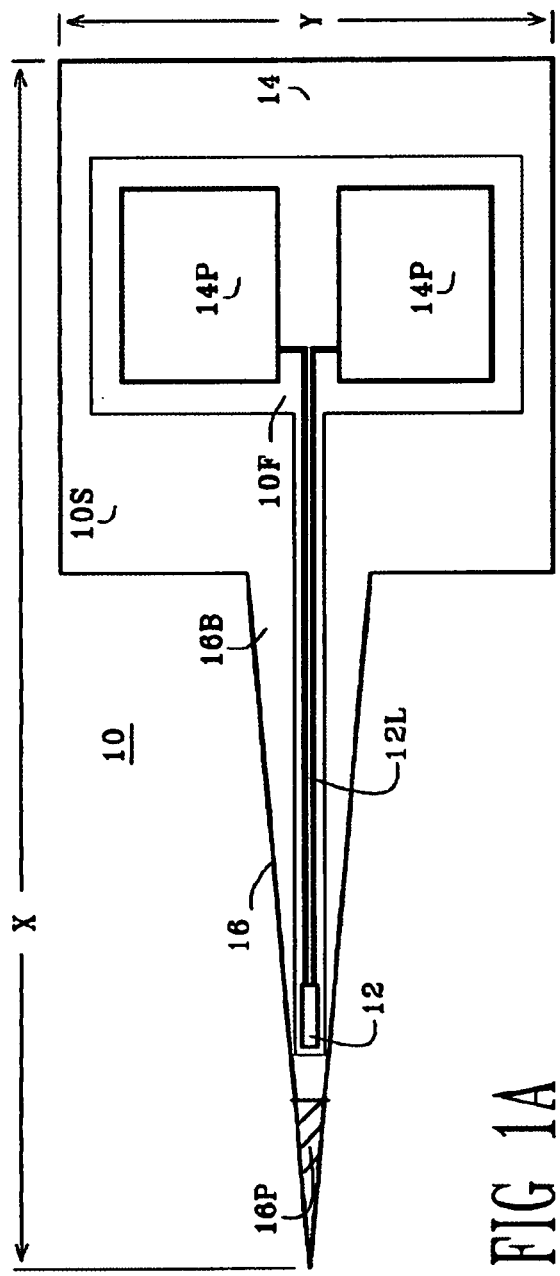
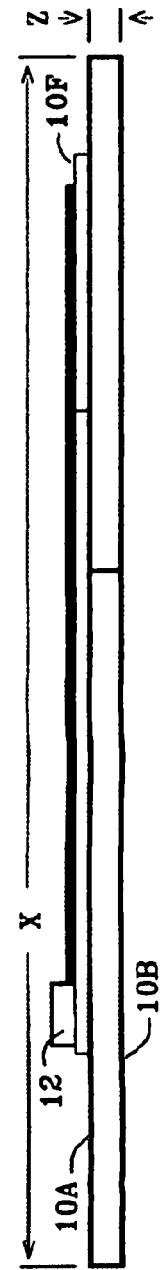
FIG 1A
FIG 1B

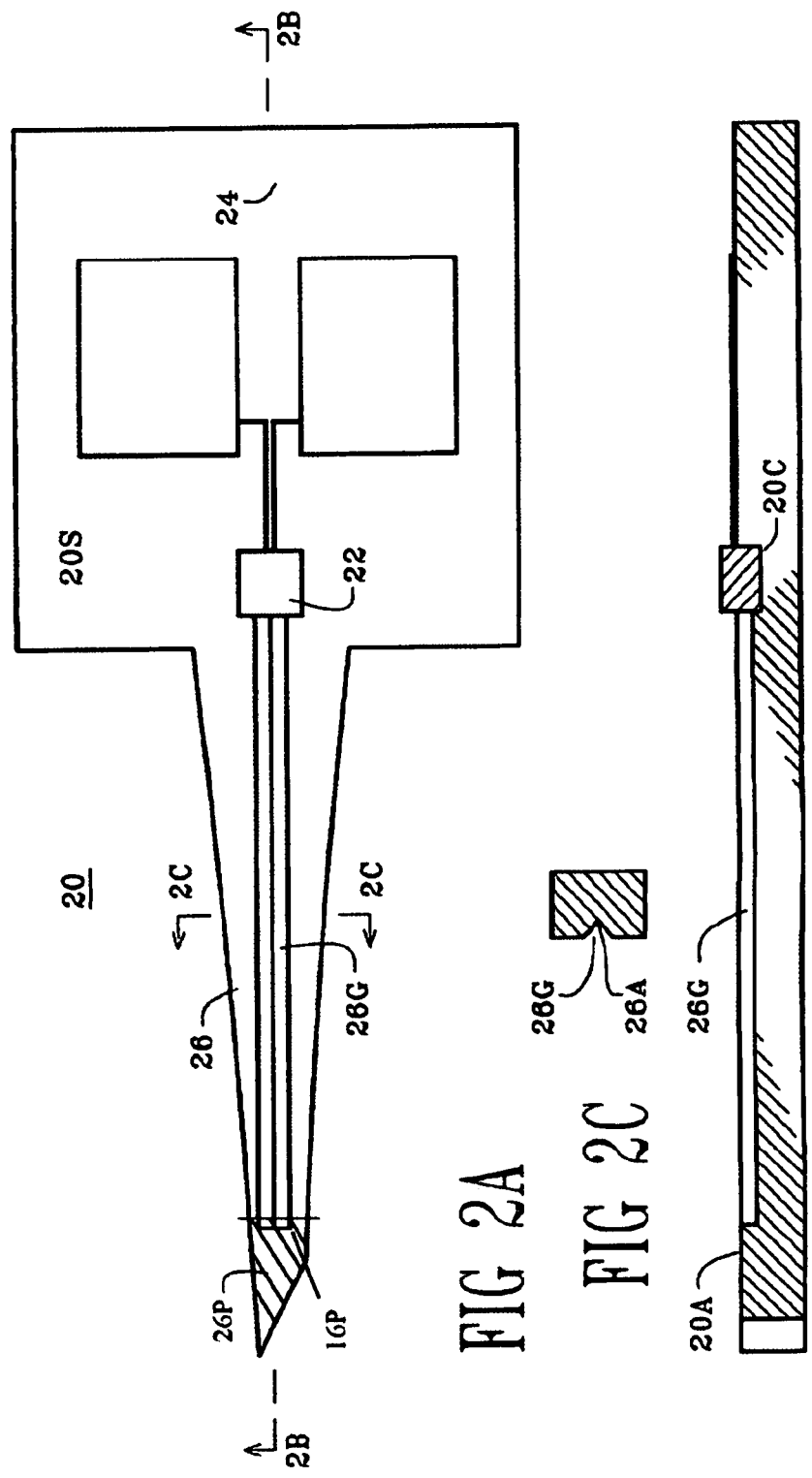

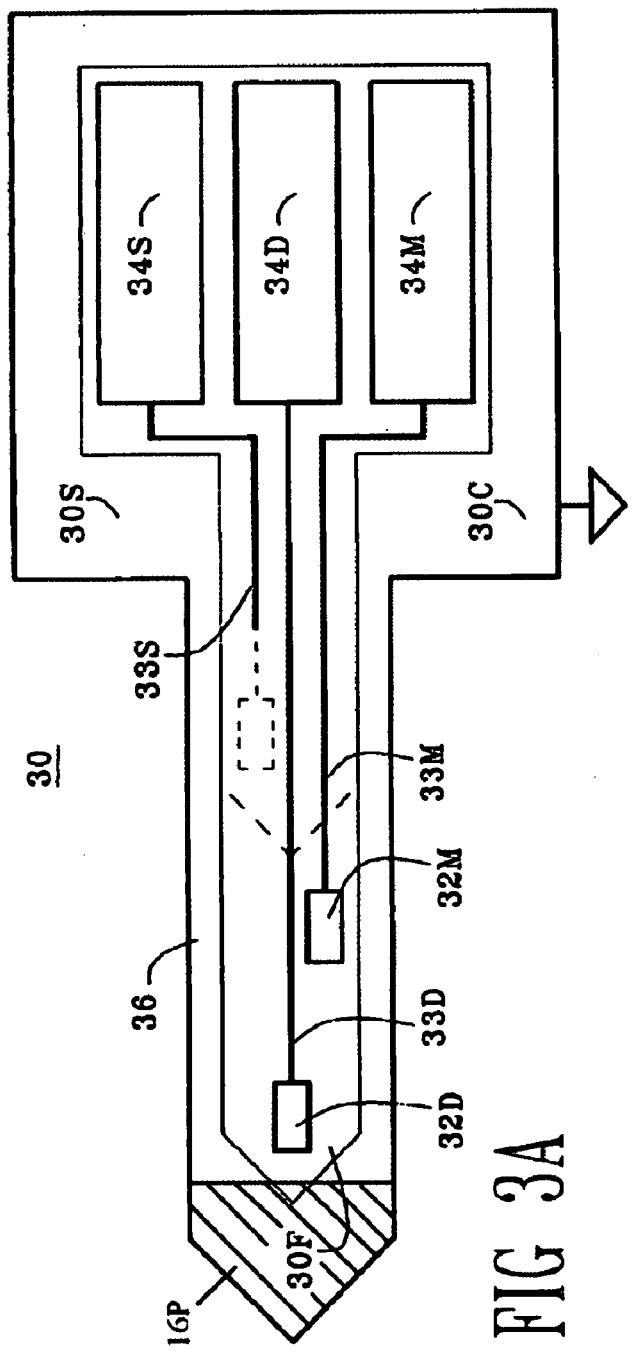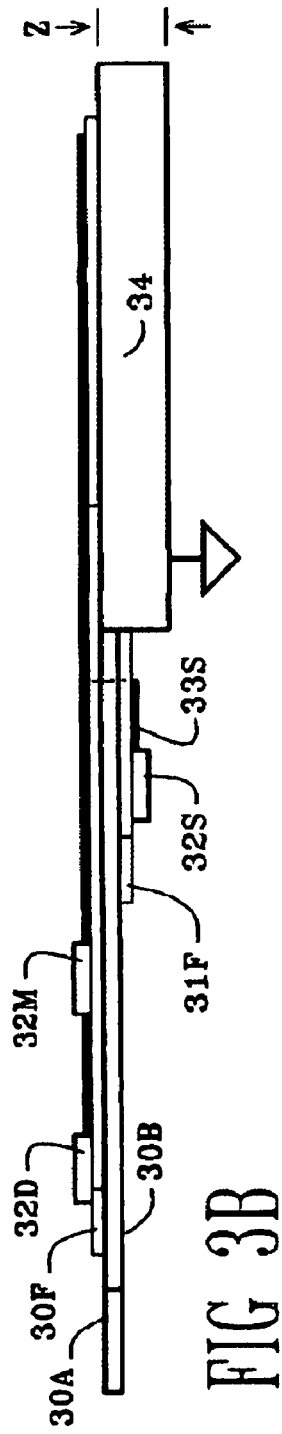
FIG 3A
FIG 3B

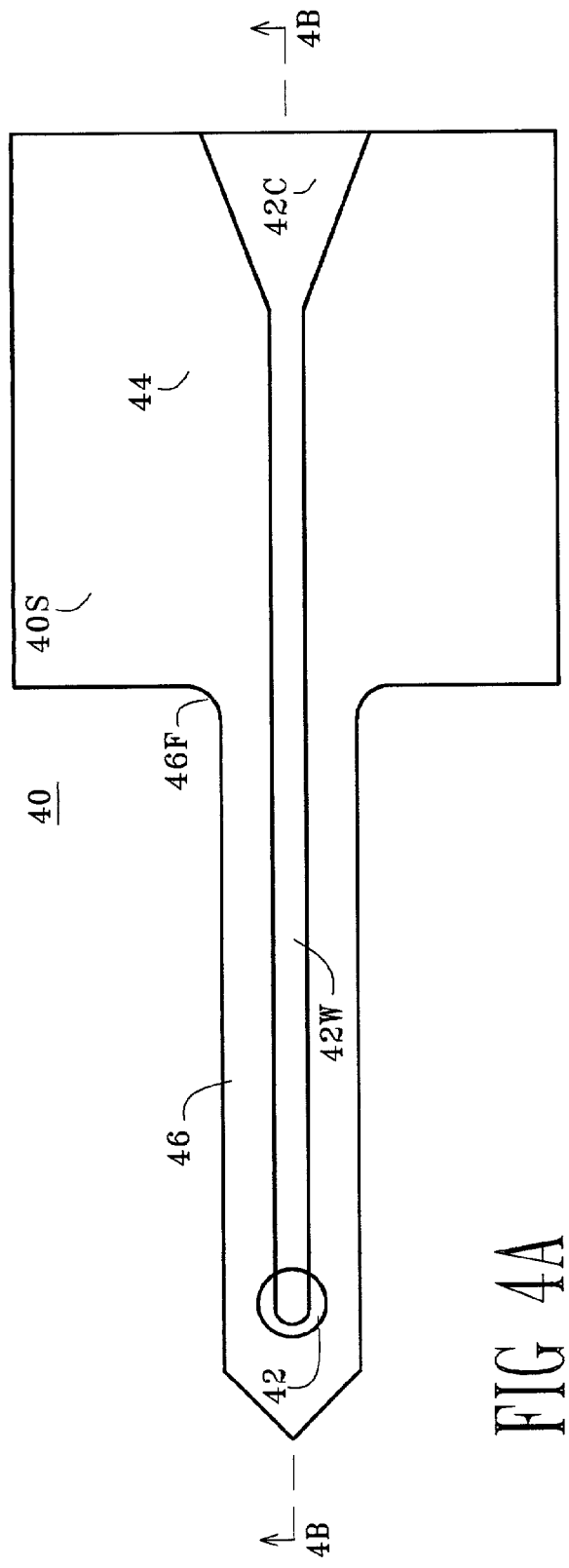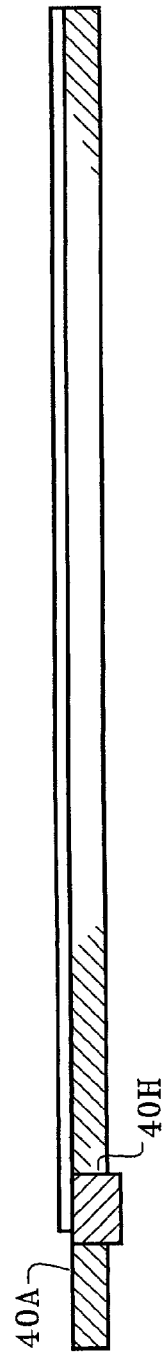
FIG 4A
FIG 4B

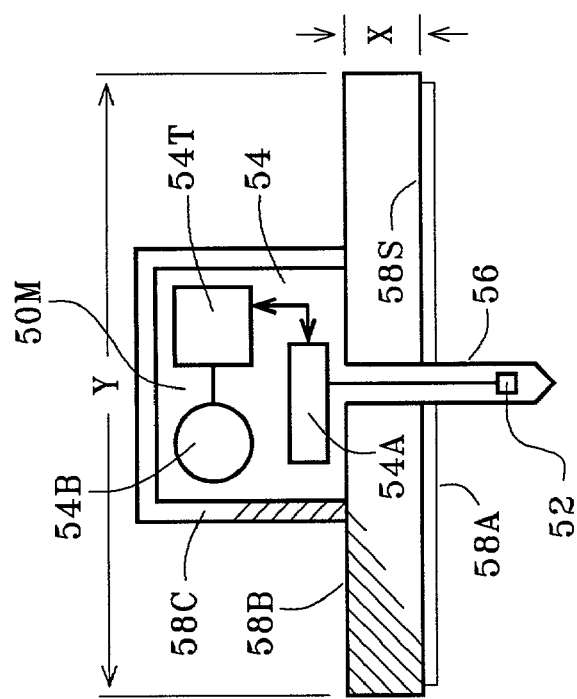
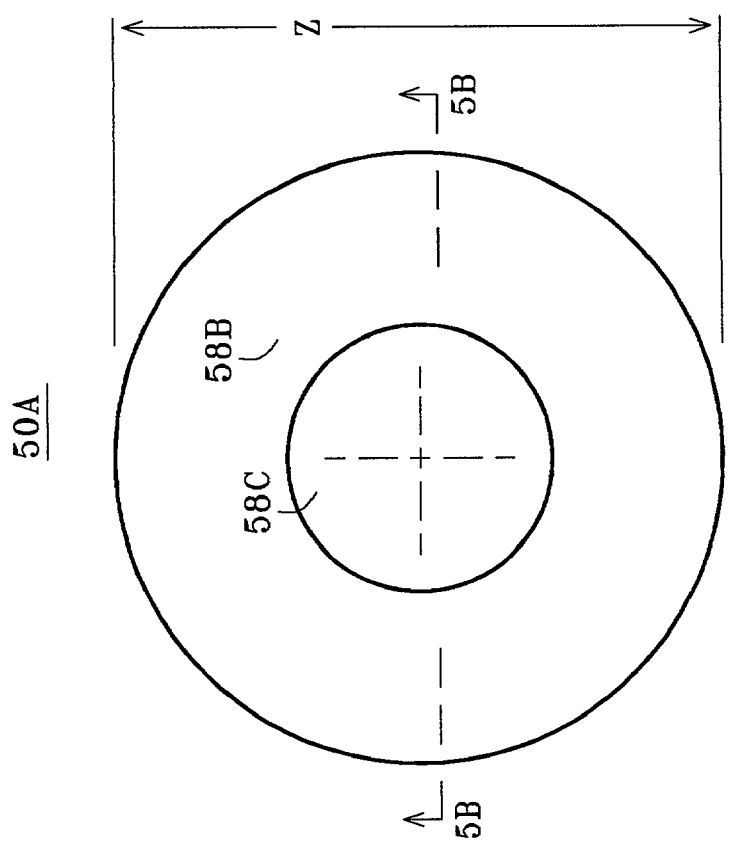
FIG 5B
FIG 5A

SILICON MICROPROBE WITH INTEGRATED BIOSENSOR

TECHNICAL FIELD

This invention relates to silicon microprobes, and more particularly to microprobes with biosensor capability incorporated therein for measuring analyte concentrations in a subject's blood, tissue, or other bodily fluids.

BACKGROUND

Diabetes mellitus is an insidious disease which affects more than 15 million Americans. About 1.5 million of these are Type I diabetics (insulin-dependent) and 12 to 14 million are Type II diabetics (noninsulin-dependent). The characteristics of diabetes include chronic and persistently high levels of glucose in blood and in urine. Although urine glucose has been used to monitor glucose levels, the measurement of blood glucose is more reliable and logistically feasible. Blood glucose has therefore become the most commonly followed clinical marker for monitoring the progress of diabetes (and other diseases) to determine treatment and control protocols. Glucose levels are routinely measured in doctors' offices, clinical laboratories, and hospitals. However, the most convenient and important measuring is in-home self-monitoring of blood glucose levels by the patients themselves to permit adjustment of the quantities of insulin and hypoglycemics administered. Such self-monitoring is known as self-monitored blood glucose. Normal blood glucose levels in humans are in the 70-100 mg/dl range and in the 160-200 mg/dl range after a heavy meal.

There are many products for diabetes related testing of glucose for diagnostic and monitoring purposes. These products range from skin swabs, reagent test strips, portable electronic meters, sensors and other instruments, lancets and needles of various shapes and sizes, syringes and other paraphernalia. Most of the currently available technologies, especially for self-monitored blood glucose measurements, are not satisfactory because they require some kind of deep lancing or finger stick with associated pain and sometimes excessive bleeding.

The smallest lancet or needle currently marketed for blood sampling has a diameter between 300 micrometers and 500 micrometers, and is constructed of stainless steel with beveled edges. Due to the large cross-section of these lancets, fingertip lancing is painful is and frequent lancing causes calluses, impairment of the use of hands, psychological trauma and other unpleasant consequences. Further, blood samples recovered from the patient must be transferred to a test strip or cartridge for assaying analyte concentrations. Obtaining blood samples by lancing and performing the analysis can be messy as well as painful for the patient.

SUMMARY

It is therefore an object of this invention to provide a miniature microprobe device with integrated analyte sensing capability. The analyte concentration is determined by a biosensor built into the microprobe, which is in data communication with an external meter via an analyte signal. A blood sample is not transferred from the subject to an external test mechanism as in the prior art. The present self-contained process minimizes messy blood smears, which is convenient for the subjects. Further, the closed nature of the present process also minimizes ambient exposure of the subject's blood. Blood may harbor undesirable biological forms (such as HIV) which could contaminate the local environment constituting a biohazard. By eliminating the blood transfer step, the present microprobe avoids such hazard.

It is another object of this invention to provide such a such a miniature microprobe device which accesses the blood and determines the analyte concentration in one simple step. The subject simply places the microprobe in a holder against the skin and waits for a signal to be sent to an external meter. The microprobe penetrates the stratum corneum (the tough outer layer of the skin) and contacts the tissue within. A separate ex vivo testing step with testing strips and the like is not required. The present one-step process eliminates the following prior art steps:

A) Preparation step in which the subject gathers required materials including a test strip or cartridge to receive the blood sample and absorbent material for controlling blood smear and leakage.

B) Transfer step in which the subject transfers the blood sample to the test strip.

C) Waste blood step in which the subject cleans-up any waste blood, and disposes of the blood D) Reset step in which the subject puts away the above material in readiness for the next blood sampling.

It is a further object of this invention to provide such a miniature microprobe device which is fabricated from a silicon wafer. A biosensor may be integrated into the surface of the microprobe. Alternately, the biosensor may be placed in a cavity in the surface of the silicon.

Silicon is compatible with integrated circuit (IC) fabrication and MEMS (microelectromechanical systems) technologies employing well established masking, deposition, etching, and high resolution photolithographic techniques. The present microprobe devices may be fabricated in mass quantities from silicon wafers through automatic IC and MEMS processing steps at minimal cost per device.

It is a further object of this invention to provide such a miniature microprobe device which minimizes subject discomfort during probe penetration and analyte measurement. The dimensions of the probe (length, width, and thickness) are very small and cause minimal tissue displacement and related lateral tissue pressure and nerve ending contact. In some cases the displacement may be so minimal that the subject feels no sensation at all during the process. For example in a clinical trial of 62 patients using a microprobe with a thickness of 100 micrometers, the majority found the insertion and retraction of the microprobe device in the arm to be painless. Of the total patients tested, 15% could not even feel the probe penetration and an additional 58% found the penetration to be barely noticeable.

It is a further object of this invention to provide such a miniature microprobe device which minimizes mechanical probe failure (breakage) during penetration and removal. Only minimal penetration effort is required due to the small probe cross-section defined by the width and thickness dimensions. These dimensions are much smaller than those of conventional metal lancets. The microprobe device retains the single-crystal structure of the silicon starting wafer and can reliably penetrate skin without breakage because of the strength provided by this single-crystal structure. The strength of the miniature probe may be further increased by optimal shaping. Data from skin puncturing tests show that the average force required to puncture the skin (0.038 Newton) is minimal compared to the buckling force required to break the probe (0.134 Newton).

It is a further object of this invention to provide such a miniature microprobe device which functions in vivo. The biosensor may be located near the probe tip for maximum penetration. The biosensors may be placed in a cavity in the surface of the silicon. The probe accesses the blood, and the analyte signal is carried along the length of the probe to the ex vivo environment by conductive leads.

It is a further object of this invention to provide such a miniature microprobe device which functions ex vivo. The biosensor may be distant from the probe on an ex vivo portion of the device, and not in direct contact with the analyte tissue. The blood is transported from the in vivo probe tip to the ex vivo portion by one or more channels.

It is a further object of this invention to provide such a miniature microprobe device which may be emplaced into the skin of the subject for a single measurement of analytes.

It is a further object of this invention to provide such a miniature microprobe device which may be installed on the subject for continuous monitoring of analytes.

It is a further object of this invention to provide such a miniature microprobe device which has multiple biosensors. The biosensor(s) may be formed by IC fabrication and are significantly smaller than the microprobe. Several biosensors may be spaced along a single microprobe for sensing several analytes per penetration, or for sensing the same analyte at different depths.

Briefly, these and other objects of the present invention are accomplished by providing a biosensor microprobe device for providing a signal to an external analyte meter. The signal indicates analyte presence in an analyte-containing fluid of a subject. The device is fabricated from a silicon wafer and has a body portion and a microprobe portion. The microprobe has a body end connected to the body portion, and having a penetration end extending away from the body portion for penetrating into the subject to access the bodily fluid. A biosensor integrated into the silicon substrate senses analyte presence and provides a signal in response to the analyte presence.

BRIEF DESCRIPTION OF THE DRAWINGS

Further objects and advantages of the present microprobe and the operation of the biosensor become apparent from the following detailed description and drawings (not drawn to scale) in which:

FIG. 1A is a plan view of in vivo microprobe device 10 showing biosensor 12 on probe 16;

FIG. 1B is a side view of device 10 of FIG. 1A;

FIG. 2A is a plan view of ex vivo device 20 showing biosensor 22 on body 24;

FIG. 2B is a sectional side view of device 20 of FIG. 2A along line 2B-2B showing biosensor 22 mounted in cavity 20C on silicon substrate 20S;

FIG. 2C is a sectional view across probe 20 of FIG. 2A along line 2C-2C showing V-groove 26G in silicon substrate 20S;

FIG. 3A is a plan view of device 30 showing multiple biosensors 32D and 32M and 32S on probe 36;

FIG. 3B is a side view of device 30 of FIG. 3A;

FIG. 4A is a plan view of device 40 showing optical biosensor 42 and waveguide 42W on probe 46;

FIG. 4B is a sectional side view of device 40 of FIG. 4A along line 4B-4B showing the optical biosensor mounted in hole 40H through silicon substrate 40S;

FIG. 5A is a plan view of microprobe assembly 50A showing cover member 58C and base member 58B;

FIG. 5B is a sectional side view of assembly 50A of FIG. 5A along line 52-5B showing transmitter 54T and battery 54B.

Figure 6:
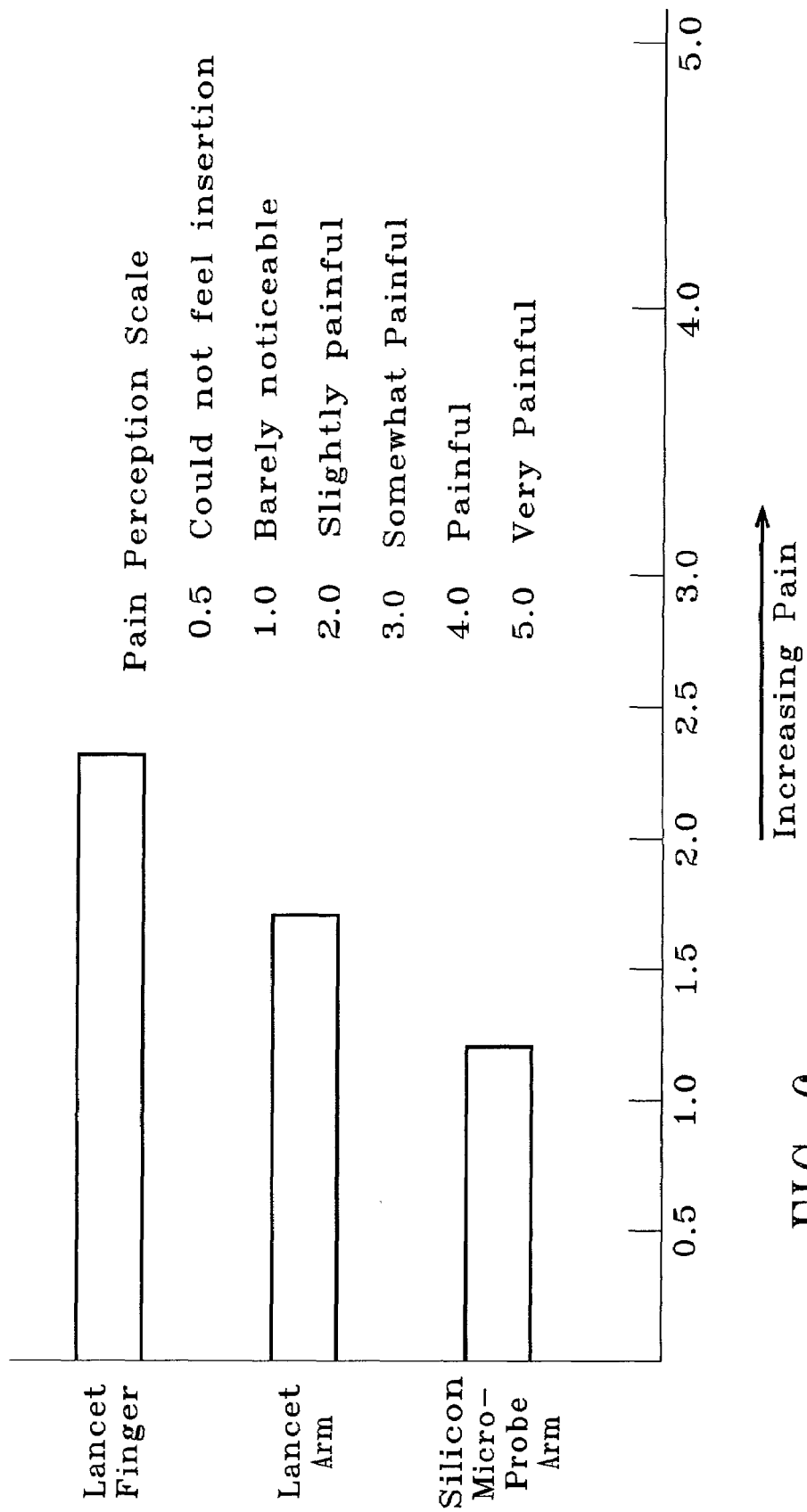
FIG. 6 is a chart comparing the average pain perception values for the silicon microprobe device with those for a conventional metal lancet.

The first digit of each reference numeral in the above figures indicates the figure in which an element or feature is most prominently shown. The second digit indicates related elements or features, and a final letter (when used) indicates a sub-portion of an element or feature.

REFERENCE NUMERALS IN DRAWINGS

The table below lists the reference numerals employed in the figures, and identifies the element designated by each numeral.

- 10 Microprobe Device 10
  - 10A Front Side 10A
  - 10F Silicon Oxide Film 10F
  - 10B Back Side 10B
  - 10S Silicon Substrate 10S
- 12 Biosensor 12
  - 12L Conductive Leads 12L
- 14 Body 14
  - 14P Electrical Interface Contact Pads 14P
- 16 Microprobe 16
  - 16B Body End 16B
  - 16P Penetration End 16P
- 20 Microprobe Device 20
  - 20A Front Side 20A
  - 20C Cavity 20C
  - 20S Silicon Substrate 20S
- 22 Biosensor 22
- 24 Body 24
- 26 Microprobe 26
  - 26A Apex 26A
  - 26G Groove 26G
  - 26P Point 26P
- 30 Device 30
  - 30A Front Side 30A
  - 30C Common Return Path 30C
  - 30F Silicon oxide layer 30F
  - 30B Back Surface 30B
  - 30S Substrate 30S
    - Multiple Biosensors 32D 32M 32S
    - Multiple Leads 33D 33M 33S
- 34 Body 34
  - Multiple interface Contacts 34D 34M 34S
- 36 Microprobe 36
- 40 Device 40
  - 40A Front side 40A
  - 40H Hole 40H
  - 40S Silicon Substrate 40S
- 42 Optical biosensor 42
  - 42C Optical Coupler 42C
  - 42W Waveguide 42W
- 44 Body 44
- 46 Microprobe 46
  - 46F Rounded Microfillet 46F
- 50A Microprobe Assembly 50A
- 50M Microprobe Device 50M
- 52 Biosensor 52
- 54 Body 54
  - 54A A/D Converter 54A
  - 54B Battery 54B
  - 54T Transmitter 54T 56 Microprobe 56
  58A Adhesive Film 58A
  58B Base Member 58B
  58C Cover Member 58C
  58S Stabilizing Surface 58S General In Vivo Embodiment (FIGS. 1A and 1B)

Microprobe device 10 provides an analyte signal from biosensor 12 to an external analyte meter (not shown) indicating analyte presence in an analyte-containing fluid of a subject (not shown). Silicon substrate 10S extends in the X length dimension, and the Y width dimension, and the Z thickness dimension, forming large body portion 14 and pointed microprobe portion 16 (as shown in FIG. 1A). The substrate has front side 10A into which the biosensor is integrated and back side 10B (as shown in FIG. 1B). The microprobe has a body end 16B connected to body 14, and a penetration end 16P extending away from the body in the X length dimension for penetrating into the subject to access the bodily fluid. A suitable signal interface structure such as electrical contact pads 14P may be deposited onto a side of silicon substrate 10S on body 14, for sliding contact connection with the analyte meter. A suitable signal carrier such as conductive leads 12L may be deposited onto a side of the silicon substrate between biosensor 12 and interface pads 14P for carrying the signal. The X length of the body may be from about 0.3 mm to about 2 mm, and the Y width of the body may be from about 0.3 mm to about 2 mm. Smaller body dimensions permit higher wafer density of microprobe devices (acreage) during manufacture.

In the in vivo embodiment the biosensor is positioned on the microprobe sufficiently distant from the body end to pass into the subject during penetration. Positioning the biosensor ex vivo affords greater flexibility in biosensor reagent selection. As shown in FIG. 1A, in vivo biosensor 12 is positioned on microprobe 16 near penetration end 16P. The biosensor accesses the analyte fluid by penetrating into the subject and contacting the fluid. The analyte fluid may be any suitable body fluid such as blood, serum, or interstitial fluid or intracellular fluid. Preferably the in vivo biosensor is located sufficiently back from the penetration end of the microprobe so as not to affect the sharpness of the point or interfere with penetration of the probe. Access may be assisted by fluid seepage along the microspace between probe and tissue up the side of the probe from the tip to the biosensor.

Diabetes monitoring is the primary focus of this disclosure for illustrative purposes. However, the microprobe device has uses in the diagnostic procedures and treatment of other diseases, emergency room status monitoring, sports medicine, veterinary medicine, research and development, with human subjects or experimental animals.

Probe Shape

The microprobe may be width tapered along the X length dimension, converging from a larger Y width dimension (of about 200 micrometers excluding the width of the microfillet portion) at the body end to a smaller Y width dimension at the penetration end. The X length of the microprobe may be from about 0.5 mm to about 2.5 mm with a penetration depth of from about 0.5 mm to about 2 mm. The discomfort or sensation experienced by the subject normally decreases with decreasing probe cross-section and length. However, a sensation floor exists where sensation is so minimal that probes smaller then this floor threshold do not offer any advantage. The taper permits easier penetration due to the gradually increasing cross-section of the probe. In addition, the taper reduces the volume of the probe causing less tissue displacement and less discomfort to the subject. The is volume of the probe may be further reduced by thinning the Z dimension (see FIG. 3B) from the initial thickness of the silicon wafer across body 34 to a slender thickness along probe 36. For example, the thickness of the silicon wafer may be from about 500 micrometers (for a 4" wafer) to about 700 micrometers (for a 6" wafer). Back side 30B of substrate 30S may be etched away to about 50 micrometers to thin the Z thickness dimension of the probe.

The convergence of the microprobe taper may be uniform (as shown in FIG. 1A) establishing a constant change in the Y width dimension and a corresponding constant decrease in the cross-section of probe 16. Alternatively, the convergence of the microprobe taper may be nonuniform (as shown in FIG. 2A) establishing a continuous change in the Y width dimension. This smooth change in width optimizes stress distribution within microprobe 26 during penetration and reduces material failure. That is, the probe is less likely to "snap-off" in the skin of the subject during use. The function for such a continuous change may be generated by stress analysis computer programs. Rounded microfillet 46F (see FIG. 4A) provides a smooth transition along the connection between body 44 and the body end of microprobe 46 which assists in eliminating stress points. The fillet transition prevents stress concentrations produced by cantilever bending of the probe. The Y width dimension of the microprobe may terminate in a suitably shaped point at the penetration end, such as symmetrically shaped point P (shown in FIG. 1A) or chisel shaped point 26P (shown in FIG. 2A)

General Ex Vivo Embodiment (FIGS. 2A, 2B and 2C)

In the ex vivo embodiment biosensor 22 is positioned on body 24 of device 20, and does not to pass into the subject during penetration. Alternatively, the biosensor may be positioned on the microprobe sufficiently close to the body end so as not to penetrate. The analyte fluid may be guided along microprobe 26 to biosensor 22 through a suitable conduit such as open fluid channel or groove 26G formed along the probe. The channel extends between the penetration end of the probe and the biosensor, and conveys the fluid by capillary action. The absence of a prior art type internal bore along the length of the probe reduces the probe diameter and simplifies probe fabrication. The open fluid channel may be a V-groove etched in the silicon of microprobe 26. The minute dimensions along apex 26A of triangular groove 26G (shown in FIG. 2C cross-section view) produce strong capillary forces that are more reliable than fluid seepage. The width and depth of V-grooves may be precisely controlled by V-groove etching IC technology. However other channel cross-sections may be produced by other techniques such as plasma etching.

Electrobiosensors (FIGS. 1A and 1B)

In general the biosensor may be an electrotype biosensor (see FIG. 1A), in which the signal is electrical energy carried on electrically conductive leads 12L and interface pads 14P. More specifically, the biosensor may be an electrochemical biosensor responsive to the analyte presence by altering the electrical energy of the signal in proportion to the concentration of the analyte presence. The analyte signal may be voltage based or current based, and may be a modulation of a quiescent value. The biosensor may be an oscillating electrogravimetric biosensor responsive to the analyte presence by altering the oscillation frequency. The magnitude of the alteration in frequency indicates the concentration of the analyte presence, and may be a.c. coupled to an analyte meter (not shown) through a suitable coupling circuit such as a capacitance device. Gravimetric devices are typically quartz crystal based and alter frequency in response to mass accumulation due to reactant buildup during the analyte sensing. Alternatively, the biosensor may be a thermal biosensor which senses heat generated in an analyte reaction, or an optical biosensor 42 (see FIG. 4A) in which senses reaction light. The light signal alterations are photon energy propagating along optical signal carrier 42W which widens into optical coupler 42C for interfacing with a meter (not shown). The optical signal carrier may be any suitable photon containment device such as a waveguide or optical fiber transparent at the photon wavelength. The biosensor may be self-luminescent or merely return incident interrogation light.

The biosensor may be integrated into the surface of the substrate, or housed in a cavity formed in the substrate or in a hole extending through the substrate. The surface of side 10A of silicon substrate 10S is planar (see FIG. 1B), and biosensor 12 is deposited onto this flat surface. Cavity 20C (see in FIG. 2B) is etched into side 20A of silicon substrate 20S. Cavity 20C extends into the silicon substrate in the Z thickness dimension. The biosensor is deposited onto the silicon within the cavity. Hole 40H (see FIG. 4B) is etched into side 40A of silicon substrate 40S. Hole 40H extends through the silicon substrate in the Z thickness dimension.

The electrotype biosensor may have a suitable electrically insulative layer such as silicon oxide film 10F (see FIG. 1A) on side 10A between conductive leads 12L and silicon substrate 10S. Silicon oxide is a better insulator than silicon, and may be employed to reduce shunt signal loss between the signal leads. Biosensor 12 is deposited on the insulative layer and is electrically isolated from the silicon substrate. The conductive leads and the conductive contacts of the electrotype biosensors may be a suitably conductive material also deposited on the insulative layer such as metal (sputtered Al Au Ti Ag W Cr for example) or carbon or doped silicon. Doped silicon leads may have a customized electrical resistance (and other characteristics) to optimize electrical features such as impedance matching or current limiting. The silicon substrate may also be sufficiently doped to form the conductive material for one of the pair of conductive leads and one of the pair of conductive contacts (see FIG. 3A).

Multiple Biosensor Embodiment (FIGS. 3A and 3B)

Multiple biosensors may be employed on a single probe. Each of these multiple biosensors may sense the presence of a different analyte. Further, each of the multiple biosensors may be positioned at a different location along the X dimension of microprobe 36 to sense analyte presence at a different penetration depth (deep, medium, and shallow). In other embodiments, multiple biosensors may sense the same analyte at different depths, or sense different analytes at the same depth. For example (see FIGS. 3A and 3B), three biosensor 32D (deep), 32M (medium), and 32S (shallow) may be deposited onto side 30A of silicon substrate 30S. These multiple biosensors require multiple conductive leads 33D, 33M, and 33S and multiple interface contacts 34D, 34M, and 34S. Silicon substrate 30S is conductive and forms common return conductive path 30C (or ground) cooperating with conductive leads 33D, 33M, and 33S and interface contacts 34D, 34M, and 34S. The return conductive path completes the electric circuit from the biosensors 32D, 32M, and 32S to an external meter and back to the biosensors. Silicon oxide layer 30F insulates the conductive return path from the source paths and source pads.

Further, the multiple biosensors may be located on either or both sides of the microprobe. Biosensor 32S is located on back side 30B on insulating layer 31F, with conductive lead 33S extending though layer 31F and substrate 30S and layer 30F to front side 30A.

Transmitter Embodiment (FIGS. 5A and 5E)

Microprobe device 50M may be sealed within a housing or cover 58C with signal transmitter 54T forming monitoring assembly 50A as shown in FIGS. 5A and 5B. The assembly is emplaced at a suitable site on the subject (not shown) for continuous monitoring of the analyte. Analyte data may be transmitted during an extended monitoring period of a few hours or several days or even weeks. Alternatively, the monitoring may be for a short period or even for a single transmission. The assembly transmits analyte concentration data to a remote meter (not shown). Preferably the emplacement site is not subject to disturbance by daily activity of the subject. The inside of the subject's arm is a convenient protected site. Microprobe portion 56 penetrates into the subject to access the analyte-containing fluid. Biosensor 52 on the microprobe senses analyte presence and provides a sensed signal in response to the analyte presence.

Base 58B extends in the Y dimension and Z dimension generally normal to the X dimension of microprobe portion 56, and forms the bottom of the assembly. Cover 58C is installed over body portion 54 of the substrate and engages base 58B for sealing the assembly. Stabilizing surface 58S forms an in vivo face of base member 58B and is disposed toward the subject when emplaced. The stabilizing surface engages the subject to maintain the penetration orientation of the microprobe portion into the subject. The stabilizing surface may have adhesive film 58A thereon for retaining the assembly at the emplacement site for the duration of the monitoring period. The adhesive holds the assembly onto the skin preventing displacement along the X dimension. The adhesive prevents the probe from working loose during the monitoring period as the subject moves around. In addition, the adhesive prevents lateral displacement of the assembly along the Y and Z dimensions. This lateral retention minimizes shear forces along the length of probe 56 preventing the probe from snapping off during subject activity. As the assembly is emplaced, the stabilizing surface engages the subject's skin and limits the penetration of the microprobe portion.

Signal transmitter 54T provides a transmitted analyte signal to a meter (not shown). Analog to digital converter 54A converts the sensed signal from the biosensor into a digital transmitted signal. A suitable power source such as battery 54B may be provided to activate the signal transmitter and the converter. The transmitter, converter and battery may be deposited into the silicon of body portion 54.

Pain Perception Testing

FIG. 6 shows the averaged response from 62 patients in a clinical trial to determine the relative pain perceived from punctures with a silicon microprobe in the arm compared with punctures in the arm and finger with conventional metal lancets. As can be seen from the FIG. 6, the punctures from the silicon microprobe were found to be noticeably less painful than those from the lancet, with the more painful of the two lancet tests being the finger stick, as expected. The test subjects repeatedly commented that the microprobe puncture was virtually painless and far more comfortable than the finger stick with the lancet.

INDUSTRIAL APPLICABILITY

It will be apparent to those skilled in the art that the objects of this invention have been achieved as described hereinbefore by providing a microprobe device with integrated analyte sensing capability, which accesses the blood and determines the analyte concentration in one simple step. The device is fabricated from a silicon wafer for compatibility with IC fabrication and MEMS technologies. Because the strength of the single-crystal structure of the starting silicon wafer is retained in the finished device, the microprobe can penetrate skin reliably without breaking. The small length, width, and thickness dimensions of the probe introduce minimal tissue displacement, rendering probe insertion and retraction essentially painless. Minimal penetration effort is required which also minimizes mechanical probe failure. The device may function in vivo or ex vivo with one or multiple biosensors, and has both single measurement and continuous monitoring applications.

CONCLUSION

Various changes may be made in the structure and embodiments shown herein without departing from the concept of the invention. For example, the various types of biosensors may be employed in either the ex vivo embodiment (FIG. 2A) or the in vivo embodiment (FIG. 1A). The stress reducing microfillet shown in the optical biosensor embodiment (FIG. 4A) may be employed in other types of biosensors. The cavity housing (FIG. 2B) and hole housing (FIG. 4B) of the biosensor may be employed in other embodiments. Further, features of embodiments shown in various figures may be employed in combination with embodiments shown in other figures. Therefore, the scope of the invention is to be determined by the terminology of the following claims and the legal equivalents thereof.

We claim:

1. A microprobe device for providing a signal to an external analyte meter indicating analyte presence in an analyte-containing bodily fluid of a subject, the microprobe device comprising:
   a silicon substrate having an X length dimension and a Y width dimension and a Z thickness dimension, and having front side and a back side extending in the X and Y dimensions;
   a body portion formed by the silicon substrate; a microprobe portion formed by the silicon substrate, having a body end connected to the body portion, and having a penetration end extending away from the body portion in the X length dimension for penetrating into the subject to access the fluids; and
   a biosensor integrated into the silicon substrate, for sensing analyte presence and for providing a signal in response to the analyte presence; and
   a silicon microfillet portion at the connection between the body end of the microprobe portion and the body portion.

2. The device of claim 1, wherein the biosensor is an optical biosensor, an electrochemical biosensor, an electrogravimetric biosensor or a thermal biosensor.

3. The device of claim 2, further comprising a signal interface structure coupled to the biosensor.

4. The device of claim 2, wherein the signal is an electrical output signal, the device further comprising: a signal interface structure and a signal carrier; wherein the signal carrier includes one or more electrically conductive leads; the signal interface structure includes one or more electrically conductive contacts.

5. The device of claim 4, wherein the interface structure is located on the surface of the body portion of the substrate, the body portion being configured to provide an electrical contact and sliding mechanical connection with an analyte meter.

6. The device of claim 1, wherein the substrate has a front surface, the biosensor is an optical biosensor or an electrochemical biosensor positioned at a location on the front surface of the body portion, the device further comprising:
   an open fluid channel formed in said substrate, the fluid channel opening along said front surface from the penetration end of the microprobe portion to the location on the body portion where the biosensor is positioned for sensing analyte presence, said open fluid channel being configured to transport the analyte-containing bodily fluid to said location by capillary action.

7. The device of claim 6, wherein the open fluid channel is uncovered over the entire length of the microprobe portion.

8. The device of claim 6, wherein the penetration end terminates in a point configured to make an incision in skin, the open fluid channel being configured to transport the analyte-containing bodily fluid from the incision to the location on the body portion where the biosensor is positioned for sensing analyte presence.

9. The device of claim 1, wherein the substrate has a front surface, the biosensor is an optical biosensor or an electrochemical biosensor positioned at a location on the front surface of the body portion, the device further comprising:
   an open fluid channel formed in said substrate, the fluid channel opening along said front surface from the penetration end of the microprobe portion to the location on the body portion where the biosensor is positioned for sensing analyte presence, said open fluid channel being configured to transport the analyte-containing bodily fluid to said location by capillary action; and
   a cover over the body portion of the substrate; the cover being adapted to engage a base to close said cover.

10. The device of claim 1, wherein the biosensor is on a surface on one side of the substrate, the biosensor being positioned on top of the surface on the body portion of the substrate, or on top of the surface on the microprobe portion near the body end, the device further comprising:
    one or more open fluid channels, each fluid channel formed in said one side of the substrate, each of the one or more fluid channels opening along the surface of said one side from the penetration end to the biosensor, each of said one or more open fluid channels being configured to transport analyte fluid to the biosensor by capillary action.

11. The device of claim 10, wherein each of the one or more open fluid channels is uncovered over any portion that passes into the subject during penetration.

12. The device of claim 10, wherein each of the one or more open fluid channels opens along the surface of said one side from a tip of the penetration end to the biosensor.

13. The device of claim 10, wherein each of the one or more open fluid channels opens along the surface of said one side from a location at the penetration end recessed behind any area of tip formation to the biosensor.

14. The device of claim 10, wherein each of the one or more open fluid channels has a V-groove cross-section.

15. The device of claim 10, wherein each of the one or more open fluid channels has a cross-section of any shape produced by plasma etching.

16. The device of claim 10, wherein the surface on the body portion of the substrate is planar.

17. The device of claim 10, further comprising a cavity wherein the biosensor is configured to be positioned over the cavity or over the open fluid channel.

18. The device of claim 1, wherein any biosensor is located sufficiently back along the microprobe portion towards the body end that it does not come into contact with any part of the penetration end so as not to affect the sharpness of a point of the penetration end or interfere with penetration of the microprobe portion into the subject.

19. The device of claim 1, wherein the microprobe portion is width tapered along the entire the X length dimension, converging continuously from a larger Y width dimension at the body end to a smaller Y width dimension at the termination of the penetration end, wherein the rate of convergence of the microprobe taper is non-uniform for optimizing stress distribution during penetration.

20. The device of claim 1, wherein the X length of the microprobe portion is from about 0.5 mm to about 2.5 mm, and the penetration depth of the microprobe portion is from about 0.5 mm to about 2 mm.

21. The device of claim 1, wherein the X length of the body portion is from about 0.3 mm to about 2 mm, and the Y width of the body portion is from about 0.3 mm to about 2 mm.

22. The device of claim 1, wherein the Y width dimension of the microprobe portion terminates in a symmetrically shaped point at the penetration end.

23. The device of claim 1, wherein the Y width dimension of the microprobe portion terminates in a chisel shaped point at the penetration end.

24. The device of claim 1, wherein the penetration end of the microprobe portion is thinner than the body portion.

25. The device of claim 1, further comprising multiple biosensors integrated into one side of the silicon substrate, wherein any subset of the multiple biosensors is located on the body portion or on the microprobe portion near the body end, and wherein the device further comprises one or more open fluid channels in the substrate for each biosensor in the subset.

26. The device of claim 1, further comprising: a base through the center of which the microprobe device is mounted, the base having a bottom face generally normal to said microprobe portion and a stabilizing surface applied to the bottom face.

27. The device of claim 26, further comprising: a cover over the body portion of the substrate, the cover engaging the base for closing said cover; and a signal transmitter configured to receive a sensed signal from the biosensor and configured to provide a transmitted electrical signal; the signal transmitter including a source of electrical power and a signal conversion capability, said signal transmitter being located on the body portion of the substrate, the base or the cover.

28. The device of claim 26, wherein the biosensor is on the body portion of the substrate, the device further comprising: an open fluid channel formed in the substrate, the fluid channel opening longitudinally along a surface of the substrate from the penetration end to the biosensor, said open fluid channel being configured to transport analyte fluid to the biosensor by capillary action.

29. The device of claim 1, further comprising a cover over the body portion of the substrate; the cover being adapted to engage a base to enclose said body portion.

30. The device of claim 1, further comprising a layer on the substrate, wherein the biosensor is deposited on the layer, the layer being an electrically insulative layer.

31. A microprobe device for providing a signal to an external analyte meter indicating analyte presence in an analyte-containing bodily fluid of a subject, comprising:
   a silicon substrate having an X length dimension and a Y width dimension and a Z thickness dimension, and having a front side and a back extending in the X and Y dimensions and a cavity extending into the silicon substrate in the Z thickness dimension
   a body portion formed by the silicon substrate;
   a microprobe portion formed by the silicon substrate, having a body end connected to the body portion, and having a penetration end extending away from the body portion in the X length dimension for penetrating into the subject to access the fluids; and
   a biosensor integrated into the silicon substrate, for sensing analyte presence and for providing a signal in response to the analyte presence, the biosensor being deposited onto the silicon within the cavity.

32. The microprobe device of claim 31, wherein the cavity extends completely through the substrate in the Z thickness dimension.

33. The device of claim 32, wherein the biosensor is in the cavity and the cavity is located on the microprobe portion near the body end or the body portion; the device further comprising:
   an open fluid channel formed in one side of the substrate, the fluid channel opening along the surface of said one side from the penetration end to the biosensor, the open fluid channel being configured to transport analyte fluid to the biosensor by capillary action.

34. The microprobe device of claim 31, wherein the silicon substrate is single crystal silicon.

35. The device of claim 31, wherein the cavity is configured to vary in all three dimensions to accommodate the size of the biosensor.

36. The device of claim 31, further comprising: a signal interface structure and a signal carrier; wherein the biosensor is an optical biosensor responsive to the analyte presence by alterations in photon energy of the signal, the signal carrier is a photon containment structure and the interface structure is an optical coupler for interfacing with a detector.

37. The device of claim 32, wherein the biosensor is integrated into a surface of a cavity opening on a surface of one side of the substrate, the cavity extending into said one side on the microprobe portion near the body end or the body portion; the device further comprising:
   an open fluid channel formed in said one side of the substrate, the fluid channel opening along the surface of said one side from the penetration end to the biosensor, the open fluid channel being configured to transport analyte fluid to the biosensor by capillary action.

38. The device of claim 37 wherein the open fluid channel is configured to transport analyte fluid to the biosensor by capillary action without a cover over any portion of the channel that passes into the subject during penetration.

39. The device of claim 37 wherein the analyte fluid is transported from a location recessed from a portion of the penetration end forming any part of a tip.

40. The device of claim 32, wherein the biosensor is in a cavity opening on a surface of one side of the substrate, the cavity extending into said one side on the microprobe portion near the body end or the body portion, the biosensor being an electrochemical biosensor or an optical biosensor configured to provide an electrical signal indicating change in analyte concentration, the device further comprising:

an interface structure and a signal carrier on or above the surface of said one side of the substrate, the signal carrier being a pair of electrically conductive leads configured to carry the signal from the biosensor to the interface structure, the interface structure being a pair of electrically conductive contacts; and an open fluid channel formed in said one side of the substrate, the fluid channel opening along said surface of said one side from the penetration end to the biosensor, the open fluid channel being configured to transport analyte fluid to the biosensor by capillary action.

41. A microprobe device for providing a signal to an external analyte meter indicating analyte presence in an analyte-containing bodily fluid of a subject, comprising:

a silicon substrate having an X length dimension and a Y width dimension and a Z thickness dimension, and having a front side and a back side extending in the X and Y dimensions;

a body portion formed by the silicon substrate;

a microprobe portion formed by the silicon substrate, having a body end connected to the body portion, and having a penetration end extending away from the body portion in the X length dimension for penetrating into the subject to access the fluids; and at least one biosensor integrated into each side of the silicon substrate, for sensing analyte presence and for providing a signal in response to the analyte presence.

42. The device of claim 41 wherein any subset of the multiple biosensors is located on the body portion or on the microprobe portion near the body end, and wherein the device further comprises one or more open fluid channels in the substrate for each biosensor in the subset.

* * * * *